(12) United States Patent
Zhou et al.

(10) Patent No.: US 12,178,441 B2
(45) Date of Patent: Dec. 31, 2024

(54) CLIP-CARTRIDGE ASSEMBLY AND CLIP APPLICATOR

(71) Applicant: Suzhou Intocare Medical Technology Co., Ltd, Jiangsu (CN)

(72) Inventors: Bingchao Zhou, Jiangsu (CN); Hui Zhang, Jiangsu (CN); Yunfeng Du, Jiangsu (CN); Dianchen Liu, Jiangsu (CN)

(73) Assignee: INTOCARE MEDICAL TECHNOLOGY (SUZHOU) CO., LTD, Jiangsu (CN)

( * ) Notice: Subject to any disclaimer, the term of this patent is extended or adjusted under 35 U.S.C. 154(b) by 829 days.

(21) Appl. No.: 17/273,045

(22) PCT Filed: Nov. 13, 2019

(86) PCT No.: PCT/CN2019/117853
§ 371 (c)(1),
(2) Date: Mar. 3, 2021

(87) PCT Pub. No.: WO2020/108298
PCT Pub. Date: Jun. 4, 2020

(65) Prior Publication Data
US 2021/0322023 A1 Oct. 21, 2021

(30) Foreign Application Priority Data
Nov. 29, 2018 (CN) .......................... 201811439575.8

(51) Int. Cl.
*A61B 17/122* (2006.01)
*A61B 17/128* (2006.01)
(Continued)

(52) U.S. Cl.
CPC ...... *A61B 17/1222* (2013.01); *A61B 17/1285* (2013.01); *A61B 2017/00398* (2013.01); *A61B 2090/035* (2016.02)

(58) Field of Classification Search
CPC ............ A61B 17/1222; A61B 17/1227; A61B 17/128; A61B 17/1225; A61B 17/068; A61B 17/10; A61B 17/08; A61B 17/083
See application file for complete search history.

(56) References Cited

U.S. PATENT DOCUMENTS 7,500,979 B2    3/2009  Hueil et al.
9,782,164 B2 *  10/2017 Mumaw ............. A61B 17/1285
(Continued)

FOREIGN PATENT DOCUMENTS

AU    2013221943 B2    9/2013
CN    101254125 A     9/2008
(Continued)

OTHER PUBLICATIONS

EP Office Action dated Aug. 20, 2021 in European application No. 19889620.1-1122/3831311.
(Continued)

*Primary Examiner* — Kathleen S Holwerda
*Assistant Examiner* — Daniel Icet
(74) *Attorney, Agent, or Firm* — McClure, Qualey & Rodack, LLP

(57) ABSTRACT

A clip-cartridge assembly and a clip applicator are provided. The clip-cartridge assembly includes a clip-cartridge, a clip delivery device, and a clip jaw provided on a side of the clip-cartridge. The clip-cartridge includes an accommodation cavity for placing a ligation clip and the clip delivery device; the clip delivery device includes an elastic member and a clip pushing block for pushing the ligation clip within the accommodation cavity to move; and if the clip jaw is
(Continued)

closed, the elastic member, by an elastic force of the elastic member, drives the clip pushing block to move in a movement direction toward the clip jaw.

17 Claims, 8 Drawing Sheets

(51) Int. Cl.
    *A61B 17/00*         (2006.01)
    *A61B 90/00*         (2016.01)

(56) References Cited

U.S. PATENT DOCUMENTS

| | | |
|---|---|---|
| 10,166,025 B2 | 1/2019 | Leimbach et al. |
| 10,682,146 B2 | 6/2020 | Rockrohr et al. |
| 10,729,449 B2 | 8/2020 | Cai et al. |
| 10,743,886 B2 | 8/2020 | Malkowski et al. |
| 2006/0255090 A1 | 11/2006 | Milliman et al. |
| 2015/0034694 A1 | 2/2015 | Cappola |

FOREIGN PATENT DOCUMENTS

| | | |
|---|---|---|
| CN | 103976771 A | 8/2014 |
| CN | 104220012 A | 12/2014 |
| CN | 104248459 A | 12/2014 |
| CN | 104414701 A | 3/2015 |
| CN | 206335487 U | 7/2017 |
| CN | 108348262 A | 7/2018 |
| EP | 3398525 A1 | 11/2018 |
| WO | 2016205184 A1 | 12/2016 |

OTHER PUBLICATIONS

International Search Report dated Feb. 12, 2020 in application PCT/CN2019/117853.

\* cited by examiner

CLIP-CARTRIDGE ASSEMBLY AND CLIP APPLICATOR

The present application claims priority of the Chinese Patent Application No. 201811439575.8 filed on Nov. 29, 2018, the disclosure of which is incorporated herein by its reference in its entirety as part of the present application.

TECHNICAL FIELD

The present disclosure relates to a clip-cartridge assembly and a clip applicator, and belongs to the field of medical instruments.

BACKGROUND

In order to fully expose a surgical visual field during a surgical operation, target tissue at an incision needs to be ligated to stop bleeding. Hemostasis technique has become one of main surgical techniques. Surgical operations on any part of human body almost without exception involve bleeding and stopping bleeding. Generally, a ligation clip applied by a clip applicator is used to clamp the target tissue so as to stop bleeding. A conventional clip applicator is usually single-firing and only applies one ligation clip at one time, and another ligation clip needs to be placed into the clip applicator after the one ligation clip clamps the target blood vessel. However, during the surgical operation, a plurality of ligation clips are required so as to stop bleeding; in this case, the conventional clip applicator has to enter and exit a puncture many times for example during an endoscopic surgical operation, which causes the time of the surgical operation to be too long, increases the bleeding amount of the patient, and adversely affects postoperative recovery of the patient.

SUMMARY

The present disclosure aims to provide a clip-cartridge assembly and a clip applicator so as to solve the problems of inconvenient operation, increased time of surgical operation and the like caused by the fact that the conventional clip applicator cannot realize continuous firing.

In order to achieve the above objects, a clip-cartridge assembly is provided by embodiments of the disclosure. The clip-cartridge assembly comprises a clip-cartridge, a clip delivery device, and a clip jaw provided on a side of the clip-cartridge. The clip-cartridge comprises an accommodation cavity for placing a ligation clip and the clip delivery device; the clip delivery device comprises an elastic member and a clip pushing block for pushing the ligation clip within the accommodation cavity to move; and if the clip jaw is closed, the elastic member, by an elastic force of the elastic member, drives the clip pushing block to move in a movement direction toward the clip jaw.

For example, the elastic member is a first spring, and the first spring and the clip jaw are respectively provided on two opposite sides of the clip pushing block.

For example, the clip-cartridge assembly further comprises a brake member, the brake member comprises a limiter and a second spring, the second spring is connected to the limiter, the limiter is provided between the clip jaw and the clip-cartridge, the limiter is movable in the accommodation cavity in a direction that is perpendicular to the movement direction of the ligation clip in the clip cavity; if the clip jaw is closed, an elastic force of the second spring drives at least a part of the limiter to exit from the accommodation cavity; and if the clip jaw is opened, the clip jaw pushes the limiter to enter into the clip-cartridge to prevent the ligation clip from entering into the clip jaw.

For example, the clip jaw comprises a first clip jaw sheet and a second clip jaw sheet, the first clip jaw sheet comprises a first jaw and a first jaw base connected to the first jaw, the second clip jaw sheet comprises a second jaw and a second jaw base connected to the second jaw; and the first jaw base, the second jaw base and the clip-cartridge are respectively provided with a first mounting groove for mounting the brake member.

For example, the limiter is a pin structure, and the second spring is sleeved on the limiter. If the clip jaw is opened, the first mounting groove of the first jaw base is misaligned with the first mounting groove of the second jaw base, the clip jaw pushes the limiter so that the limiter moves into the accommodation cavity to prevent the ligation clip from entering into the clip jaw, and the second spring is compressed. If the clip jaw is closed, the first jaw and the second jaw move toward each other, the first mounting groove of the first jaw base is aligned with the first mounting groove of the second jaw base, an elastic force of the second spring drives at least a part of the limiter to exit from the accommodation cavity, the limiter is accommodated in the first mounting groove so that the ligation clip enters into the clip jaw under the driving of the first spring.

For example, the first jaw and the second jaw are provided with a positioning groove; and after entering into the clip jaw, the ligation clip is accommodated in the positioning groove.

For example, a mounting part is provided on the clip-cartridge, a bump is provided on the mounting part, the clip jaw is provided with a second mounting groove matching with the bump, and the bump is inserted into the second mounting groove so that the clip jaw is mounted onto the mounting part.

For example, the second mounting groove is provided on the first jaw base and the second jaw base, and a torsion spring for driving the clip jaw to open is provided in the second mounting groove.

For example, an outer sleeve is sleeved on the clip-cartridge; the outer sleeve has a diameter larger than sizes of the first jaw base and the second jaw base if the clip jaw is opened, and the outer sleeve has the diameter smaller than sizes of the first jaw and the second jaw in an opening direction of the clip jaw if the clip jaw is opened; and if the clip jaw is closed, the first jaw and the second jaw are closed and partially provided in the outer sleeve.

A clip applicator is provided by the embodiments of the disclosure. The clip applicator further comprises the clip-cartridge assembly as described above, a firing device, a driving device, and a control circuit. The firing device comprises a pushing rod, the pushing rod is connected to the driving device and the clip-cartridge, the pushing rod is provided on a side of the clip-cartridge away from the clip jaw; and the control circuit is configured to control the driving device to drive the pushing rod to reciprocate between the clip-cartridge and the driving device, so as to drive the clip-cartridge to move and then control opening or closing of the clip jaw.

For example, the clip applicator further comprises a working head, the pushing rod and the driving device are provided in the working head, the working head and the outer sleeve are connected to each other by a connecting member, the connecting member comprises a connecting tube connected to the working head, a sliding groove is provided on the connecting tube, a protrusion is provided on a side of the outer sleeve close to the working head, and the protrusion is slid into the sliding groove and clamped with the sliding groove to connect the working head and the outer sleeve.

For example, the sliding groove is L-shaped, and the protrusion is slid into the sliding groove longitudinally and then rotates to be clamped with the sliding groove.

For example, the connecting member further comprises a latching element provided in the connecting tube, and the latching element limits the protrusion in the sliding groove.

For example, the latching element comprises a sleeve provided in the connecting tube, a buckle is provided on the sleeve, a slot matching with the buckle is provided on the outer sleeve, and the firing rod passes through the sleeve and is connected to the clip-cartridge.

For example, the connecting member further comprises an actuator for driving the sleeve to move toward the outer sleeve so that the buckle is inserted into the slot.

For example, the actuator is an elastic member, the elastic member is fixed in the connecting tube; and during the protrusion is clamped in the sliding groove, the elastic member is compressed.

For example, the driving device comprises an input shaft, a driving gear provided on the input shaft, a nut engaging with the driving gear, and a threaded rod connected to the nut; the driving device further comprises a limiting block, the limiting block is respectively connected to the threaded rod and the pushing rod, and the pushing rod is rotatable relative to the limiting block.

Compared with the prior art, the beneficial effects of the embodiments of the present disclosure at least are as follows. The clip-cartridge assembly of the embodiments of the present disclosure is provided with the elastic member to push the clip pushing block to move toward the clip jaw, thereby ensuring that the clip pushing block pushes the ligation clip into the clip jaw under the action of the elastic force to realize continuous firing of the ligation clips. The clip applicator of the embodiments of the present disclosure uses the clip-cartridge assembly which is combined with the firing device, the driving device, and the control circuit, so that the control circuit controls the driving device to drive the pushing rod and then drive the clip-cartridge to move to realize the opening and closing of the clip jaw. In addition, for the clip applicator, the pushing rod is provided in the working head, the clip-cartridge is provided in the outer sleeve, and the pushing rod is connected to the clip-cartridge, so as to facilitate the driving device to control the firing of the clip jaw. This design makes the working head reusable, and the working head is capable of being installed with the clip-cartridges of different specifications to meet the requirements of the surgical operation, which greatly reduces the cost and the number of surgical instruments.

The above description is only an outline of the technical solutions of the embodiments of the present disclosure. In order to better understand the technical solutions of the embodiments of the present disclosure so that they can be implemented according to the contents of the specification, the following detailed description will be made with the exemplary embodiments of the present disclosure in conjunction with the accompanying drawings.

DETAILED DESCRIPTION

Figure 1:
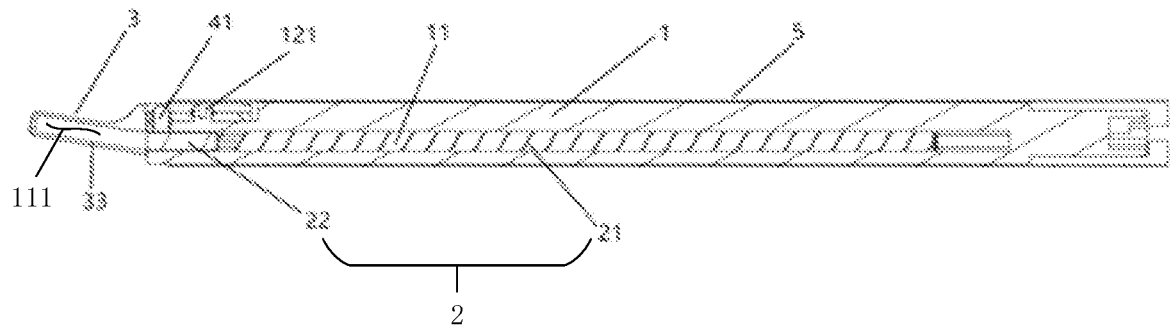
FIGS. 1 and 2 are schematic structural diagrams of a clip-cartridge assembly according to embodiments of the present disclosure.

The exemplary specific modes of the present disclosure will be described in further detail below in conjunction with the drawings and embodiments. The following embodiments are intended to illustrate the present disclosure, but not to limit the scope of the present disclosure.

It should be noted that the terms such as "upper", "lower", "left", "right", "inner", "outer" and the like in the present disclosure are only intended to describe the embodiments of the present disclosure by referring to the drawings, and are not used as limiting terms.

Figure 2:
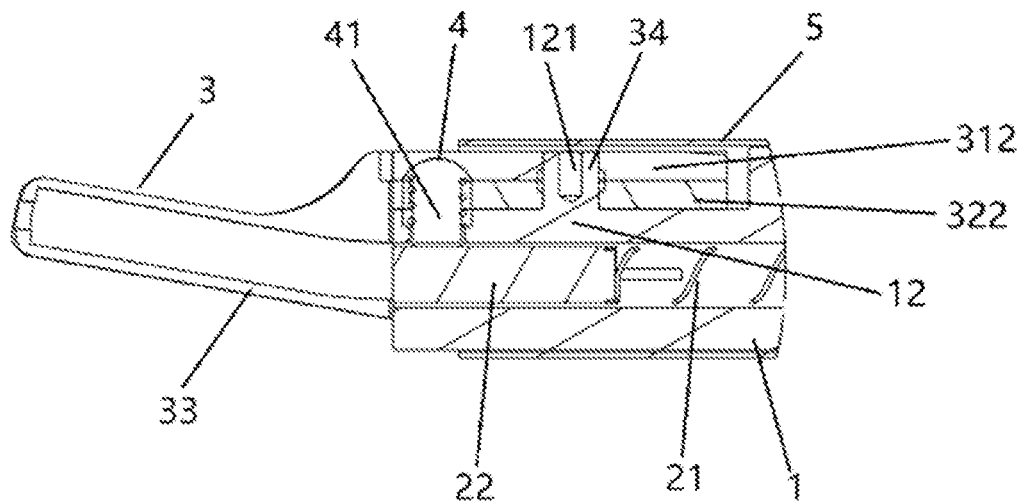
Figure 3:
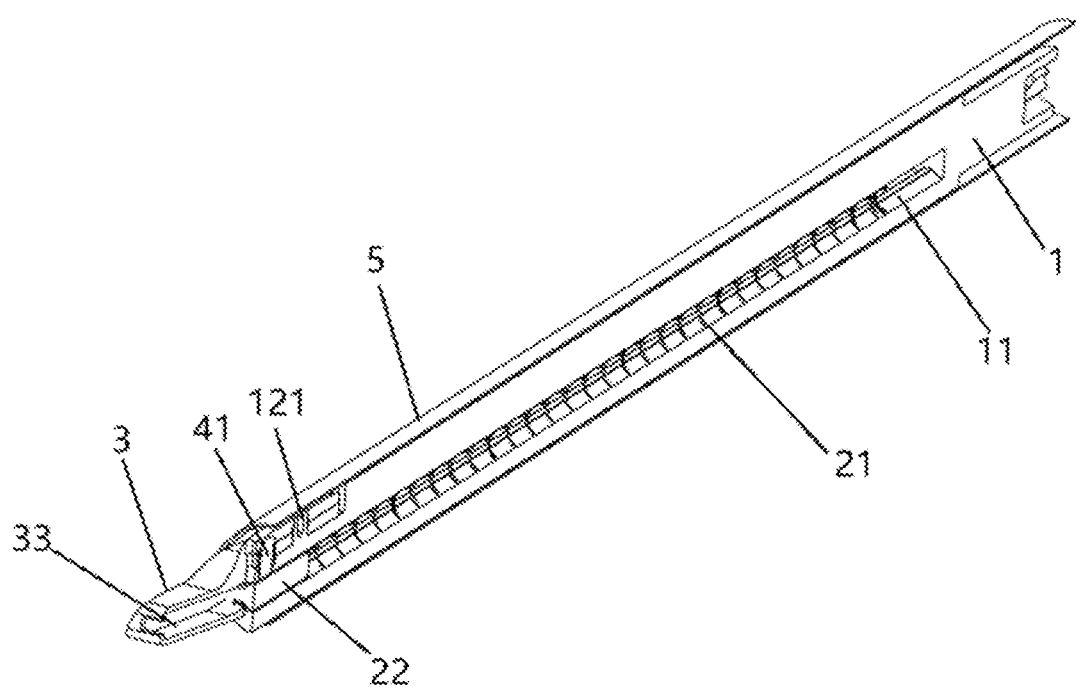
FIG. 3 is a cross-sectional diagram of the clip-cartridge assembly according to the embodiments of the present disclosure.
Figure 4:
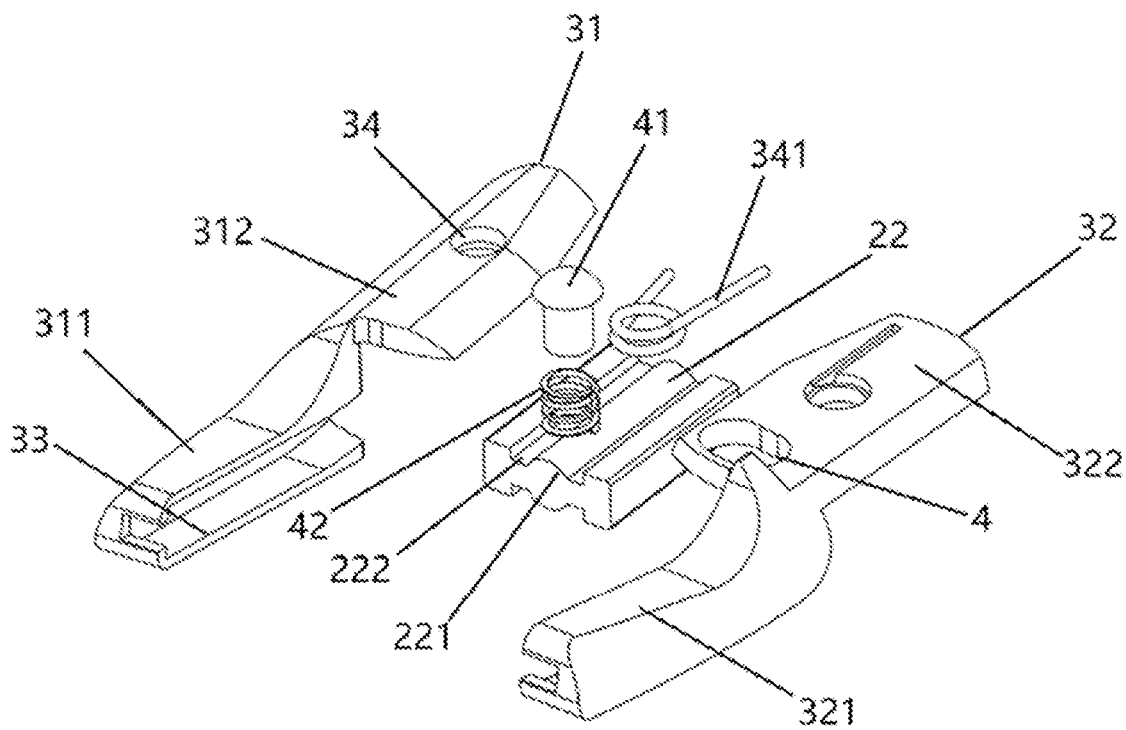
FIGS. 4 and 5 are schematic structural diagrams of a clip jaw of the clip-cartridge assembly according to the embodiments of the present disclosure.
Figure 5:
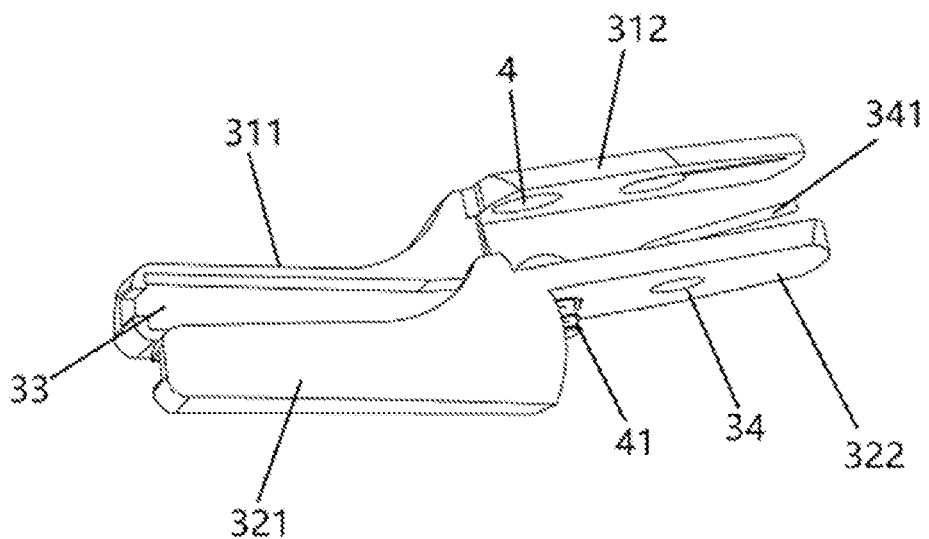
Figure 6:
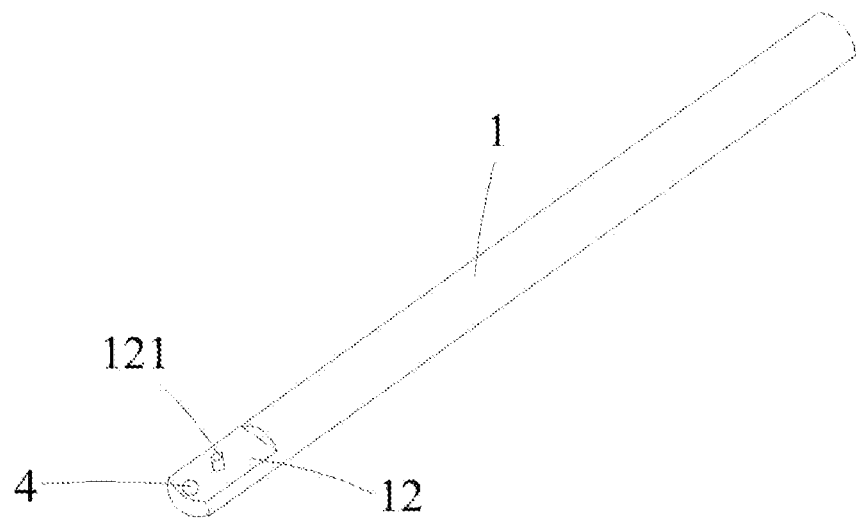
FIG. 6 is a schematic structural diagram of a clip-cartridge of the clip-cartridge assembly according to the embodiments of the present disclosure.

Referring to FIGS. 1 to 6, a clip-cartridge assembly provided by embodiments of the present disclosure comprises a clip-cartridge 1, a clip delivery device 2, and a clip jaw 3 provided on a side of the clip-cartridge 1. The clip-cartridge 1 comprises an accommodation cavity 11 for placing a ligation clip 111 and the clip delivery device 2. The clip delivery device 2 comprises an elastic member 21 and a clip pushing block 22 for pushing the ligation clip 111 within the accommodation cavity 11 to move. If the clip jaw 3 is closed, the elastic member 21, by an elastic force of the elastic member 21, drives the clip pushing block 22 to move in a movement direction toward the clip jaw 3.

In the present disclosure, the elastic member 21 is preferably a first spring. The first spring 21 and the clip jaw 3 are respectively provided on two opposite sides of the clip pushing block 22, and the first spring 21 is fixed on the other side of the clip-cartridge 1. In an initial state, a length of the first spring 21 is smaller than a length of the accommodation cavity 11. Preferably, the length of the first spring 21 in a free state is a difference of the length of the accommodation cavity 11 and a length of the clip pushing block 22. After the ligation clip is mounted into the accommodation cavity 11, the clip pushing block 22 is provided on a side of the ligation clip away from the clip jaw 3 in the accommodation cavity 11, and the first spring 21 is compressed.

By the foregoing arrangement, the ligation clips in the clip-cartridge 1 can be automatically continuously fired, and the total number of the ligation clips that are provided in the clip-cartridge 1 is not limited in theory. However, there is a problem that the next ligation clip is easily pushed into the clip jaw by the clip pushing block after the previous ligation clip is fired. Therefore, the clip-cartridge assembly according to the embodiments of the disclosure is further provided with a brake member for limiting a position of the next ligation clip. The brake member comprises a limiter 41 and a second spring 42. The second spring 42 is connected to the limiter 41. The limiter 41 is provided between the clip jaw 3 and the clip-cartridge 1. The limiter 41 is movable in the accommodation cavity 11 in a direction that is perpendicular to the movement direction of the ligation clip in the accommodation cavity 11.

In the embodiments of the present disclosure, the limiter 41 for example is a pin structure. The second spring 42 is sleeved on the limiter 41. The second spring 42 for example is a compression spring. The brake member is provided as follows. The clip jaw 3 comprises a first clip jaw sheet 31 and a second clip jaw sheet 32. The first clip jaw sheet 31 comprises a first jaw 311 and a first jaw base 312 connected to the first jaw 311. The second clip jaw sheet 32 comprises a second jaw 321 and a second jaw base 322 connected to the second jaw 321. The first jaw base 312, the second jaw base 322, and the clip-cartridge 11 are respectively provided with a first mounting groove 4 for mounting the brake member. For example, the first mounting groove 4 of the second jaw base 322 penetrates through the second jaw base 322 to have upper and lower openings; the first mounting groove 4 of the first jaw base 312 is only provided at a bottom surface of the first jaw base 312 to adapt to a size of the limiter 41 but does not penetrate through a top surface of the first jaw base 312. The brake member works as follows. If the clip jaw 3 is opened, the first mounting groove 4 of the first jaw base 312 is misaligned with the first mounting groove 4 of the second jaw base 322, the bottom surface of the first jaw base 312 pushes the limiter 41 so that the limiter 41 moves downward and to be a block in the accommodation cavity 11, thereby preventing the ligation clip from entering into the clip jaw 3, and the second spring 42 is compressed; if the clip jaw 3 is closed, the first jaw 311 and the second jaw 321 move toward each other, the first mounting groove 4 of the first jaw base 312 is aligned with the first mounting groove 4 of the second jaw base 322, an elastic force of the second spring 42 drives at least a part of the limiter 41 to exit from the accommodation cavity 11, the limiter 41 is accommodated in the first mounting groove 4 so that the ligation clip enters into the clip jaw 3 under the driving of the first spring 21, and the second spring 42 is in the free state.

In the embodiments of the present disclosure, the first mounting groove 4 of the second jaw base 322 for example is provided wider in a direction perpendicular to a movement direction of the limiter to prevent the limiter 41 from being broken due to being pressed. The first jaw 311 and the second jaw 321 are provided with a positioning groove 33. After entering into the clip jaw 3, the ligation clip is accommodated in the positioning groove 33.

In the embodiments of the present disclosure, a mounting part 12 is further provided on the clip-cartridge 1. A bump 121 is provided on the mounting part 12. The clip jaw 3 is provided with a second mounting groove 34 matching with the bump 121. The bump 121 is inserted into the second mounting groove 34 so that the clip jaw 3 is mounted onto the mounting part 12. For example, the second mounting groove 34 is provided on the first jaw base 312 and the second jaw base 322. A torsion spring 341 for driving the clip jaw 3 to open is provided in the second mounting groove 34. If the clip jaw 3 is closed, the torsion spring 341 is compressed; the compressed torsion spring 341 tends to drive the first clip jaw sheet 31 and the second clip jaw sheet 32 to move away from each other so that the clip jaw 3 is opened. An outer sleeve 5 is sleeved on an outside of the clip-cartridge 1. The outer sleeve 5 has a diameter larger than sizes of the first jaw base 312 and the second jaw base 322 after the clip jaw 3 is closed. The outer sleeve 5 has the diameter smaller than sizes of the first jaw 311 and the second jaw 312 in an opening direction of the clip jaw 3 after the clip jaw 3 is opened. This ensures that if the clip jaw 3 is pulled inward, the opened first jaw 311 and the opened second jaw 312 enter into the outer sleeve 5 only after being closed.

In the embodiments of the present disclosure, the clip pushing block 22 is an irregular structure. For example, the clip pushing block 22 is cuboid-like as a whole, the clip pushing block 22 is provided with a smooth arch structure 221 on the top of the clip pushing block 22, and the clip pushing block 22 is provided with a recess 222 on both sides of the arch structure 221. In this way, the arch structure 221 is connected to the first spring 21 to avoid uneven force applied on the clip pushing block 22; and the recess 222 is provided on both sides of the arch structure to facilitate pushing of the ligation clip. Of course, in other embodiments, the structure of the clip pushing block 22 may be designed according to actual requirements.

Figure 7:
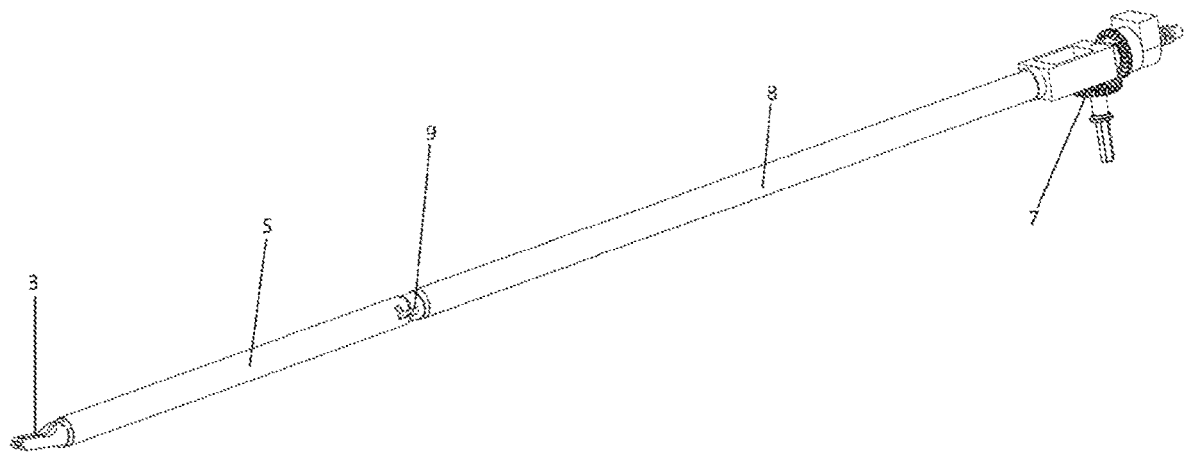
FIGS. 7 and 8 are schematic structural diagrams of a clip applicator according to the embodiments of the present disclosure.
Figure 8:
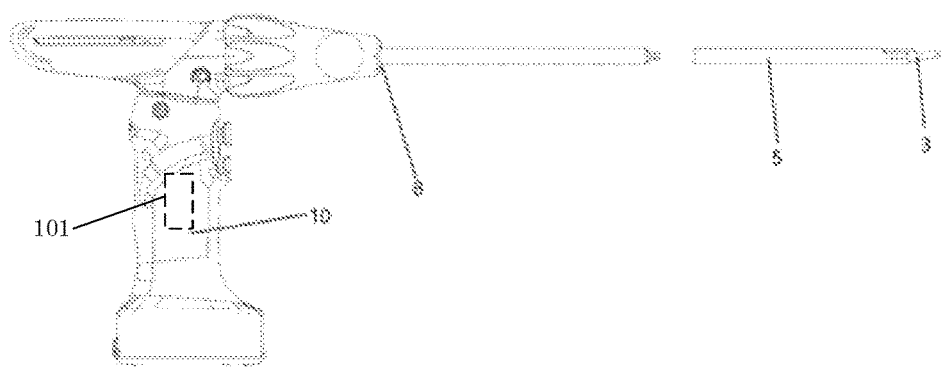
Figure 9:
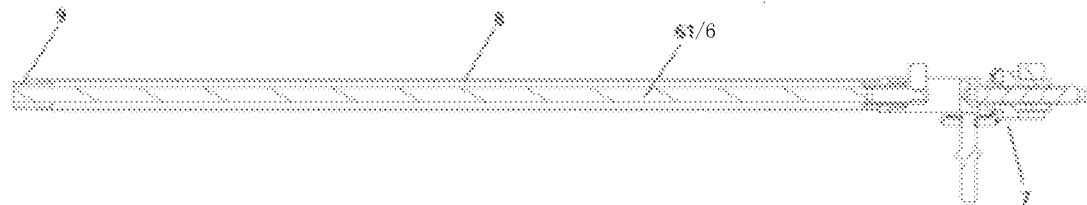
FIG. 9 is a cross-sectional diagram of a firing device and a driving device of the clip applicator according to the embodiments of the present disclosure.
Figure 10:
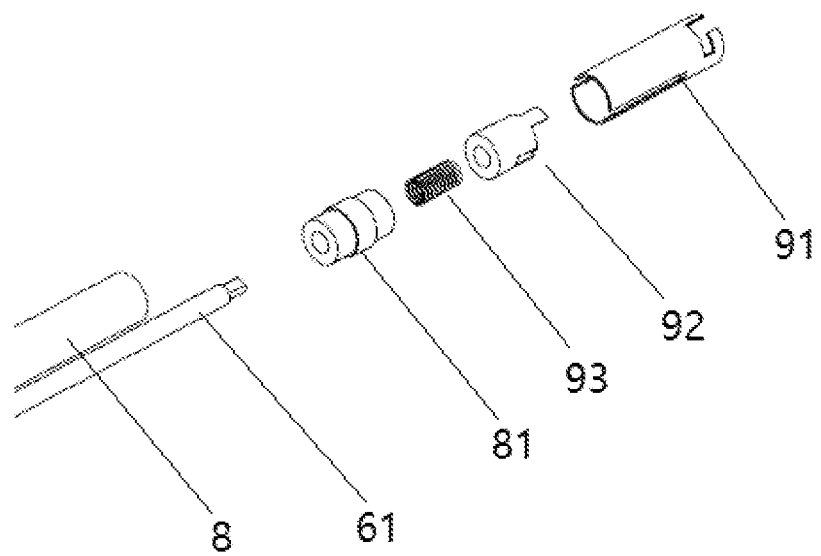
FIGS. 10 to 12 are schematic structural diagrams of a connecting member of the clip applicator according to the embodiments of the present disclosure.
Figure 11:
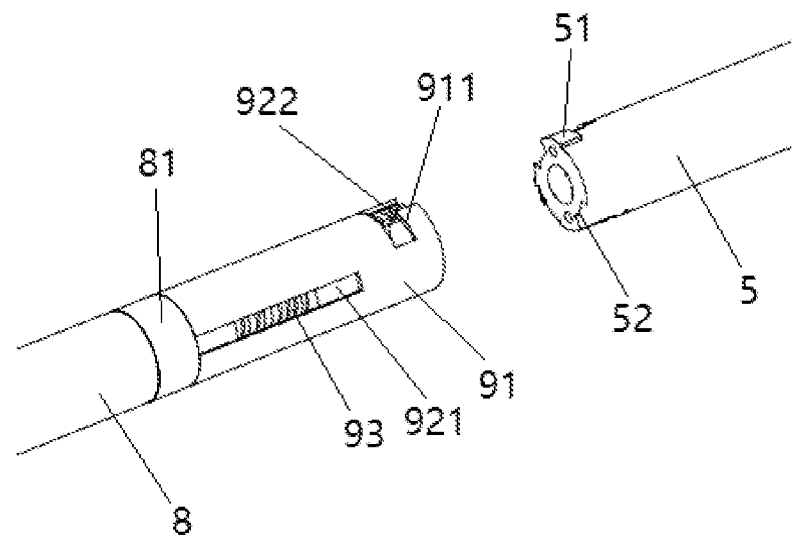
Figure 12:
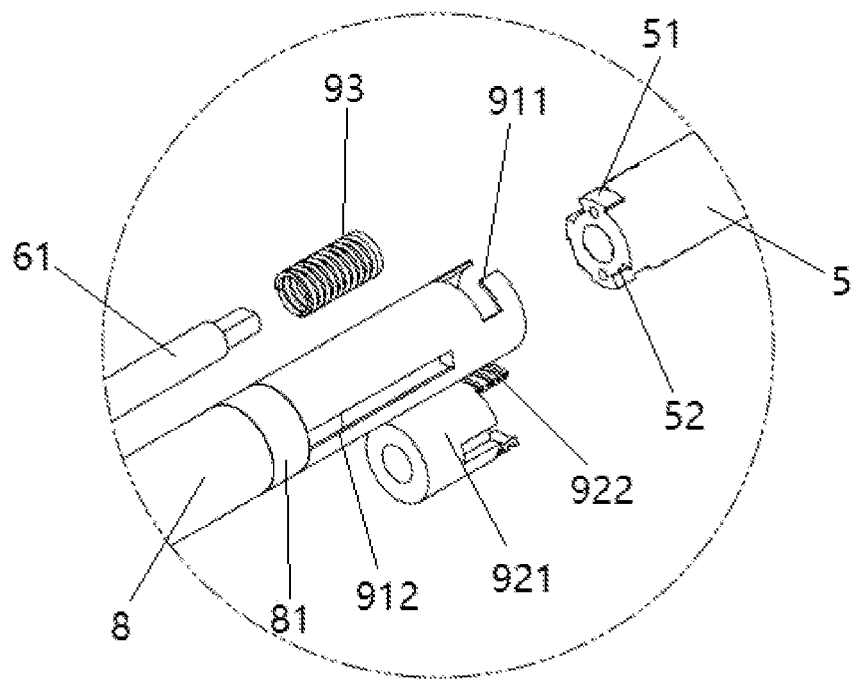
Figure 13:
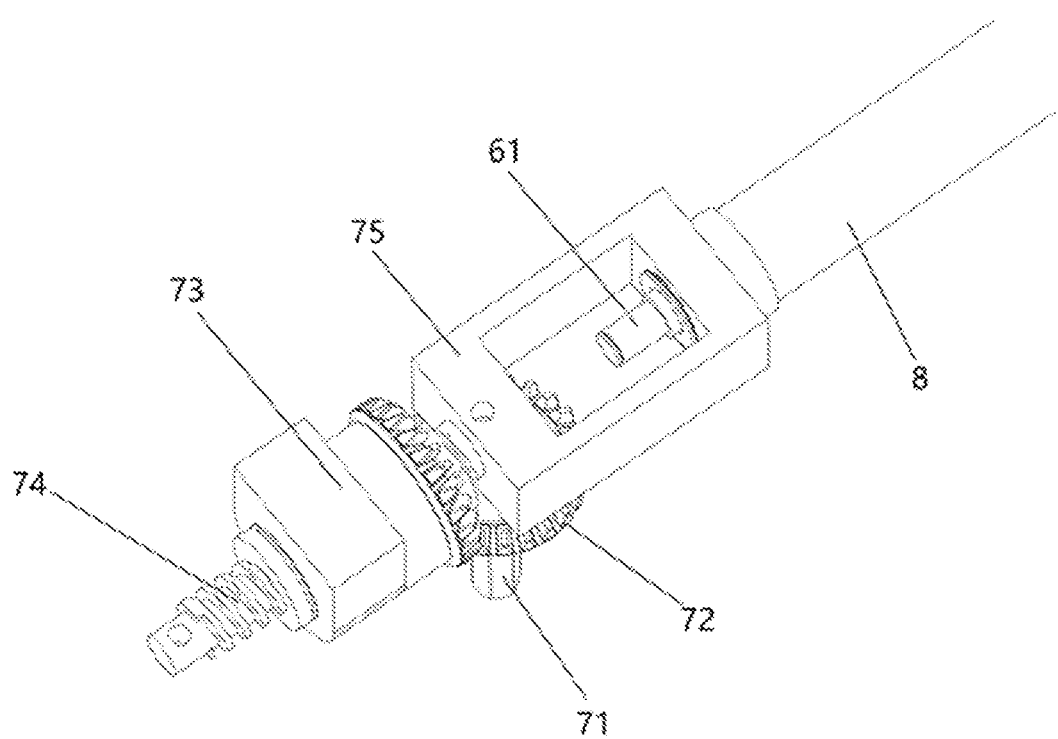
FIG. 13 is a schematic structural diagram of the driving device of clip applicator according to the embodiments of the present disclosure.

Referring to FIGS. 7 to 13, a clip applicator is provided by the embodiments of the present disclosure, and the clip applicator comprises the clip-cartridge assembly as described above, a firing device 6, a driving device 7, and a control circuit 101. The firing device 6 comprises a pushing rod. Two ends of the pushing rod 61 are connected to the driving device 7 and the clip-cartridge 1, respectively. The pushing rod 61 is provided on a side of the clip-cartridge 1 away from the clip jaw 3. The control circuit 101 is connected to the driving device 7 and is configured to control the driving device 7 to drive the pushing rod 61 to reciprocate between the clip-cartridge 1 and the driving device 7, thereby driving the clip-cartridge 1 to move, and then controlling the opening and closing of the clip jaw 3.

For example, the pushing rod 61 is provided in a working head 8. The working head 8 and the outer sleeve 5 are connected to each other by a connecting member 9. The connecting member 9 comprises a connecting tube 91 connected to the working head 8. A sliding groove 911 is provided on the connecting tube 91. The outer sleeve 5 is provided with a protrusion 51 on a side close to the working head 8. The protrusion 51 is slid into the sliding groove 911 and clamped with the sliding groove 911 to connect the working head 8 and the outer sleeve 5. The connecting member 9 is a hollow structure so that the pushing rod 61 passes through the connecting member 9 to be connected to the clip-cartridge 1. By the design as described above, the working head 8 provided with the pushing rod 61 can be used all the time without being replaced, and the clip-cartridge assemblies of different models and specifications can be mounted onto the working head 8 for surgery.

In the embodiments of the present disclosure, the connecting tube 91 is integral with the working head 8, or the connecting tube 91 and the working head 8 are provided separately and then the connecting tube 91 is connected to the working head 8. In the embodiments, for example, the connecting tube 91 and the working head 8 are provided separately; the connecting tube 91 is connected to the working head 8 by a connecting sleeve 81; and a connection manner is a snap-fit manner or a thread manner. Preferably, the sliding groove 911 is L-shaped; the protrusion 51 is slid into the sliding groove 911 longitudinally and then rotates laterally to be clamped with the sliding groove 911 to realize the connection between the working head 8 and the outer sleeve 5. Of course, in other embodiments, the shape of the sliding groove 911 may be selected according to actual requirements, as long as the working head 8 and the outer sleeve 5 are connected to each other; and the shape of the sliding groove 911 is not limited herein.

In the embodiments of the present disclosure, the connecting member 9 further comprises a latching element 92 provided in the connecting tube 91, and the latching element 92 comprises a sleeve 921 provided in the connecting tube 91. A buckle 922 is provided on the sleeve 921. A slot 52 matching with the buckle 922 is provided on the outer sleeve 5. Preferably, two slots 52 and two protrusions 51 are provided; correspondingly, two buckles 922 and two sliding grooves 911 are provided. The connecting member 9 further comprises an actuator 93 for driving the sleeve 921 to move toward the outer sleeve 5 so that the buckle 922 is inserted into the slot 52. The actuator 93 is an elastic element, and is preferably a spring structure. The actuator 93 is fixed in the connecting tube 91 and connected to the sleeve 921. During the outer sleeve 5 is connected to the working head 8, the protrusion 51 is clamped in the sliding groove 911, and the actuator 93 is compressed. During the outer sleeve 5 is separated from the working head 8, the actuator 93 resets the sleeve 921.

For example, the outer sleeve 5 is connected to the working head 8 by the connecting member 9 as follows: the outer sleeve 5 and the working head 8 are in a separated state, the buckle 922 is located at an opening of the connecting tube 91, and is preferably aligned with an opening of the sliding groove 911; then during the outer sleeve 5 is connected to the working head 8, the protrusion 51 on the outer sleeve 5 is slowly slid into the sliding groove 911, the buckle 922 is pushed toward the inside of the connecting tube 91 by the protrusion 51 and the actuator 93 is compressed, and then the protrusion 51 is rotated counterclockwise to be clamped with the sliding groove 911 and the buckle 922 is slid into the slot 52 on the outer sleeve 5. The separation and disassembly of the outer sleeve 5 and the working head 8 by the connecting member 9 is as follows: the latching element 92 is manually pressed and moved backward through a long groove 912 or the sliding groove 911 provided on the connecting tube 91 and the outer sleeve 5 is rotated clockwise so that the protrusion 51 slides out of the sliding groove 911 to realize the separation of the working head 8 and the outer sleeve 5, and the latching element 92 is reset under the action of the actuator 93.

In the embodiments of present disclosure, the outer sleeve 5 and the working head 8 are firmly connected to each other by the clamping manner. Of course, in other embodiments, the outer sleeve 5 and the working head 8 may be detachably connected by a thread manner or other manners depending on the actual requirements.

In the embodiments of the present disclosure, the driving device 7 is provided in the working head 8. The driving device 7 comprises an input shaft 71, a driving gear 72 provided on the input shaft 71, a nut 73 engaging with the driving gear 72, and a threaded rod 74 connected to the nut 73. The nut 73 is a hollow structure with internal threads. The threaded rod 74 passes through the hollow structure and is connected to the nut 73 by the internal threads. The driving device further comprises a limiting block 75. The threaded rod 74 and the pushing rod 61 are respectively provided on two sides of the limiting block 75 and are rotatable relative to the limiting block 75. The limiting block 75 is connected to the threaded rod 74 and fixed in the working head 8 to ensure that the limiting block 75 and the nut 73 do not rotate when the pushing rod 61 rotates.

In the embodiments of the present disclosure, the clip applicator further comprises a handle 10. The control circuit 101 is provided in the handle 10. The control circuit comprises a motor control module, a working head identification module, a clip delivery and clip firing control module, a battery detection and control module, a working status indicator module and a data record storage module that are controlled by a single-chip processor.

In the control circuit 101:

The motor control module is configured for controlling the switching-on and switching-off of the input shaft 71. A closing/opening button (not shown) mounted at a lower portion of the handle 10 is isolated from an inner part of the main body of the clip applicator, and the motor control is realized by a magnet inside the button being close to or away from a Hall switch sealed and packaged in the handle;

The working head identification module transmits the data about the type of the working head by a terminal (not shown) provided on the connecting member 9, and then the control circuit starts a corresponding working program based on the data;

The clip delivery and clip firing control module, together with a signal identification module, a photoelectric limit switch position control module, and a safety module that are mounted in the working head 8, realizes the delivery of the ligation clip and the firing of the ligation clip;

The battery detection and control module provides a battery power detection function, and monitors the battery power before and during the surgical operation to ensure that the battery power used during the surgical operation meets the needs of the surgical operation or the battery is replaced in time;

The working status indicator module provides a status of the battery power, a working head connection status, a status of completing the delivery of the ligation clip, and a status of completing the firing of the ligation chip by a display.

The clip applicator of the embodiments of the present disclosure operates as follows. In an initial state, the clip jaw 3 is closed, the limiter 41 moves into the first mounting groove 4 under the action of the second spring 42; the clip pushing block 22 in the accommodation cavity 11 is provided at a position away from the clip jaw 3; because of the actions of the first spring 21 and the clip pushing block 22, one ligation clip enters into the positioning groove 33 of the clip jaw 3. The opening button provided on the handle 10 is pressed, the clip jaw 3 is opened under the action of the pushing rod 61, at this time, the limiter 41 moves into the first mounting groove to prevent the next ligation clip from entering into the clip jaw 3; after the ligation clip reaches a position of a target blood vessel or a target tissue, by pressing the closing button on the handle 10, the pushing rod 61 drives the clip-cartridge 1 to move back so that the clip jaw 3 is closed to complete the firing of the ligation clip, at this time, the limiter 41 moves into the first mounting groove 4 under the action of the second spring 42, and the next ligation clip is pushed into the positioning groove 33 under the actions of the first spring 21 and the clip pushing block 22. Then the previous procedures are repeated to complete the cycle of closing of the clip jaw and firing of the ligation clip ->opening of the clip jaw ->delivery of the clip jaw.

Compared with the prior art, the beneficial effects of the embodiments of the present disclosure at least are as follows. The clip-cartridge assembly of the embodiments of the present disclosure is provided with the elastic member to push the clip pushing block to move toward the clip jaw, thereby ensuring that the clip pushing block pushes the ligation clip into the clip jaw under the action of the elastic force to realize continuous firing of the ligation clips. The clip applicator of the embodiments of the present disclosure uses the clip-cartridge assembly which is combined with the firing device, the driving device, and the control circuit, so that the control circuit controls the driving device to drive the pushing rod and then drive the clip-cartridge to move to realize the opening and closing of the clip jaw. In addition, for the clip applicator, the pushing rod is provided in the working head, the clip-cartridge is provided in the outer sleeve, and the pushing rod is connected to the clip-cartridge, so as to facilitate the driving device to control the firing of the clip jaw. This design makes the working head reusable, and the working head is capable of being installed with the clip-cartridges of different specifications to meet the requirements of the surgical operation, which greatly reduces the cost and the number of surgical instruments.

In addition, the clip applicator of the embodiments of the present disclosure works automatically, is electrically driven and does not rely on the experience and status of a doctor; therefore, the stability of a ligation effect is good, and the doctor does not need to fire manually, which saves the doctor's physical strength, time and effort.

The technical features of the foregoing embodiments may be combined arbitrarily. In order to make the description concise, all possible combinations of the various technical features in the foregoing embodiments are not described. However, as long as there is no conflict in the combination of these technical features, all combinations should be considered as within the scope of the disclosure.

The foregoing embodiments merely are some of the embodiments of the present disclosure and the descriptions of the foregoing embodiments are specific and detailed, but the foregoing embodiments should not be understood as limiting of the scope of the disclosure. It should be pointed out that a person of ordinary skill in the art may make modifications and improvements without departing from the concept of the present disclosure, and all of these modifications and improvements belong to the protection scope of the present disclosure. Therefore, the protection scope of the present disclosure should be defined by the appended claims.

What is claimed is:

1. A clip-cartridge assembly, comprising a clip-cartridge, a clip delivery device, and a clip jaw provided on a side of the clip-cartridge, wherein
the clip-cartridge comprises an accommodation cavity for placing a ligation clip and the clip delivery device;
the clip delivery device comprises an elastic member and a clip pushing block for pushing the ligation clip within the accommodation cavity to move; and
if a distal end of the clip jaw is closed, the elastic member, by an elastic force of the elastic member, drives the clip pushing block to move in a movement direction toward the clip jaw from a proximal end of the clip jaw;
wherein the elastic member is a first spring, and the first spring and the clip jaw are respectively provided on two opposite sides of the clip pushing block;
the clip-cartridge assembly further comprises a brake member, the brake member comprises a limiter and a second spring, the second spring is connected to the limiter, the limiter is provided between the clip jaw and the clip-cartridge, the limiter is movable in the accommodation cavity in a direction that is perpendicular to a movement direction of the ligation clip in the accommodation cavity;
meantime, if the distal end of the clip jaw is closed, an elastic force of the second spring drives at least a part of the limiter to exit from the accommodation cavity; and
if the distal end of the clip jaw is opened, the proximal end of the clip jaw pushes the limiter to enter into the accommodation cavity to prevent a next ligation clip from entering into the clip jaw from the proximal end of the clip jaw.

2. The clip-cartridge assembly according to claim 1, wherein
the clip jaw comprises a first clip jaw sheet and a second clip jaw sheet, the first clip jaw sheet comprises a first jaw and a first jaw base connected to the first jaw, the second clip jaw sheet comprises a second jaw and a second jaw base connected to the second jaw; and
the first jaw base, the second jaw base and the clip-cartridge are respectively provided with a first mounting groove for mounting the brake member.

3. The clip-cartridge assembly according to claim 2, wherein
the first jaw and the second jaw are provided with a positioning groove; and
after entering into the clip jaw, the ligation clip is accommodated in the positioning groove.

4. The clip-cartridge assembly according to claim 2, wherein a mounting part is provided on the clip-cartridge, a bump is provided on the mounting part, the clip jaw is provided with a second mounting groove matching with the bump, and the bump is inserted into the second mounting groove so that the clip jaw is mounted onto the mounting part.

5. The clip-cartridge assembly according to claim 4, wherein the second mounting groove is provided on the first jaw base and the second jaw base, and a torsion spring for driving the clip jaw to open is provided in the second mounting groove.

6. The clip-cartridge assembly according to claim 2, wherein the first mounting groove of the second jaw base penetrates through the second jaw base; the first mounting groove of the first jaw base is only provided at a surface of the first jaw base but does not penetrate through the first jaw base.

7. The clip-cartridge assembly according to claim 1, wherein the limiter is a pin structure, and the second spring is sleeved on the limiter.

8. The clip-cartridge assembly according to claim 1, wherein
an outer sleeve is sleeved on the clip-cartridge;
the outer sleeve has a diameter larger than sizes of the first jaw base and the second jaw base if the clip jaw is closed, and the outer sleeve has the diameter smaller than sizes of the first jaw and the second jaw in an opening direction of the clip jaw if the clip jaw is opened; and
if the clip jaw is closed, the first jaw and the second jaw are closed and partially provided in the outer sleeve.

9. The clip-cartridge assembly according to claim 1, wherein the clip pushing block is provided with a smooth arch structure on a top of the clip pushing block, and the clip pushing block is provided with a recess on both sides of the arch structure.

10. A clip applicator, comprising a clip-cartridge assembly, a firing device, a driving device, and a control circuit, wherein the clip-cartridge assembly comprises:
a clip-cartridge, a clip delivery device, and a clip jaw provided on a side of the clip-cartridge, wherein the clip-cartridge comprises an accommodation cavity for placing a ligation clip and the clip delivery device;

the clip delivery device comprises an elastic member and a clip pushing block for pushing the ligation clip within the accommodation cavity to move; and if a distal end of the clip jaw is closed, the elastic member, by an elastic force of the elastic member, drives the clip pushing block to move in a movement direction toward the clip jaw from a proximal end of the clip jaw;

wherein the elastic member is a first spring, and the first spring and the clip jaw are respectively provided on two opposite sides of the clip pushing block;

the clip-cartridge assembly further comprises a brake member, the brake member comprises a limiter and a second spring, the second spring is connected to the limiter, the limiter is provided between the clip jaw and the clip-cartridge, the limiter is movable in the accommodation cavity in a direction that is perpendicular to a movement direction of the ligation clip in the accommodation cavity;

meantime, if the distal end of the clip jaw is closed, an elastic force of the second spring drives at least a part of the limiter to exit from the accommodation cavity; and if the distal end of the clip jaw is opened, the proximal end of the clip jaw pushes the limiter to enter into the accommodation cavity to prevent a next ligation clip from entering into the clip jaw from the proximal end of the clip jaw;

the firing device comprises a pushing rod, two ends of the pushing rod are connected to the driving device and the clip-cartridge, respectively, the pushing rod is provided on a side of the clip-cartridge away from the clip jaw; and the control circuit is connected to the driving device and configured to control the driving device to drive the pushing rod to reciprocate between the clip-cartridge and the driving device, so as to drive the clip-cartridge to move and then control opening or closing of the distal end of the clip jaw.

11. The clip applicator according to claim 10, wherein the clip applicator further comprises a working head, the pushing rod and the driving device are provided in the working head, the working head and an outer sleeve are connected to each other by a connecting member, the connecting member comprises a connecting tube connected to the working head, a sliding groove is provided on the connecting tube, a protrusion is provided on a side of the outer sleeve sleeved on the clip-cartridge, which is close to the working head, and the protrusion is slid into the sliding groove and clamped with the sliding groove to connect the working head and the outer sleeve.

12. The clip applicator according to claim 11, wherein the sliding groove is L-shaped, and the protrusion is slid into the sliding groove longitudinally and then rotates to be clamped with the sliding groove.

13. The clip applicator according to claim 11, wherein the connecting member further comprises a latching element provided in the connecting tube, and the latching element limits the protrusion in the sliding groove.

14. The clip applicator according to claim 13, wherein the latching element comprises a sleeve provided in the connecting tube, a buckle is provided on the sleeve, a slot matching with the buckle is provided on the outer sleeve, and the pushing rod passes through the sleeve and is connected to the clip-cartridge.

15. The clip applicator according to claim 14, wherein the connecting member further comprises an actuator for driving the sleeve to move toward the outer sleeve so that the buckle is inserted into the slot.

16. The clip applicator according to claim 15, wherein the actuator is an elastic member, the actuator is fixed in the connecting tube; and during the protrusion is clamped in the sliding groove, the actuator is compressed.

17. The clip applicator according to claim 10, wherein the driving device comprises an input shaft, a driving gear provided on the input shaft, a nut engaging with the driving gear, and a threaded rod connected to the nut;

the driving device further comprises a limiting block, the limiting block is respectively connected to the threaded rod and the pushing rod, and the pushing rod is rotatable relative to the limiting block.

* * * * *